United States Patent
Parthasaradhi et al.

(10) Patent No.: US 7,238,686 B2
(45) Date of Patent: Jul. 3, 2007

(54) POLYMORPHS OF QUETIAPINE FUMARATE

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Kesireddy Subash Chander, Hyderabad (IN)

(73) Assignee: Hetero Drugs Limited, Hyderabad, IN (US)

( * ) Notice: Subject to any disclaimer, the term of this patent is extended or adjusted under 35 U.S.C. 154(b) by 0 days.

(21) Appl. No.: 10/488,628

(22) PCT Filed: Mar. 3, 2003

(86) PCT No.: PCT/IN03/00043

§ 371 (c)(1), (2), (4) Date: Mar. 3, 2004

(87) PCT Pub. No.: WO2004/078735

PCT Pub. Date: Sep. 16, 2004

(65) Prior Publication Data

US 2004/0242562 A1    Dec. 2, 2004

(51) Int. Cl.
C07D 281/16   (2006.01)
A61K 31/55    (2006.01)

(52) U.S. Cl. .................... 514/211.13; 540/551
(58) Field of Classification Search .......... 514/211.13; 540/551
See application file for complete search history.

(56) References Cited

U.S. PATENT DOCUMENTS

| | | | | |
|---|---|---|---|---|
| 4,879,288 A | * | 11/1989 | Warawa et al. | 514/211.13 |
| 6,372,734 B1 | * | 4/2002 | Snape | 514/211.13 |
| 2002/0147186 A1 | * | 10/2002 | Snape | 514/211.13 |
| 2003/0216376 A1 | * | 11/2003 | Lifshitz-Liron et al. | 514/211.13 |
| 2004/0220400 A1 | * | 11/2004 | Diller et al. | 540/551 |

OTHER PUBLICATIONS

Flohr, M.J.K. "X-ray Powder Diffraction" USGS information Handout [online], May 1997 [retrieved Aug. 9, 2006]. Retrieved from the Internet: pubs.usgs.gov/info/diffraction/html/index.html.

* cited by examiner

*Primary Examiner*—Brenda Coleman
(74) *Attorney, Agent, or Firm*—Caesar, Rivise, Bernstein, Cohen & Pokotilow, Ltd.

(57) ABSTRACT

The present invention relates to novel polymorphic forms of quetiapine fumarate, processes for their preparation and pharmaceutical compositions containing them.

17 Claims, 3 Drawing Sheets

POLYMORPHS OF QUETIAPINE FUMARATE

RELATED APPLICATIONS

This application is a national stage entry under 35 U.S.C. § 371 of PCT/IN03/00043, filed Mar., 3, 2003.

FIELD OF THE INVENTION

The present invention relates to novel polymorphic forms of quetiapine fumarate, processes for their preparation and pharmaceutical compositions containing them.

BACKGROUND OF THE INVENTION

2-[2-(4-Dibenzo[b,f]-[1,4]thiazepin-11-yl-1-piperazinyl)ethoxy]ethanol (quetiapine) and its salts were disclosed in Eur. Pat. No. 0240228 and they are useful for their anti-dopaminergic activity, for example, as an antipsychotic or neuroleptic.

Various processes for preparation of quetiapine and 2-[2-(4-Dibenzo[b,f]-[1,4]thiazepin-11-yl-1-piperazinyl)ethoxy]ethanol hemifumarate (quetiapine fumarate) were described in EP 0240 228, EP 0282236, WO 01/55125 and WO 99/06381. According to the teachings of literature, quetiapine fumarate was crystallized from ethanolic solution containing quetiapine free base and fumaric acid. Quetiapine fumarate prepared according this method fails to produce well defined reproducible crystalline form.

It has now been discovered stable, reproducible two crystalline forms of quetiapine fumarate. It has also been discovered that the crystalline forms of quetiapine fumarate can be obtained in very pure state. Thus, they can be used as active ingredients in pharmaceutical preparations.

Thus, the object of the present invention is to provide quetiapine fumarate in stable and reproducible crystalline forms, processes for their preparation and pharmaceutical composition containing them.

The present invention also provides amorphous form of quetiapine with adequate stability and good dissolution properties.

Thus another object of the present invention is to provide amorphous form of quetiapine fumarate, a process for preparing it and a pharmaceutical composition containing it.

DETAILED DESCRIPTION OF THE INVENTION

The present invention provides a novel crystalline form of quetiapine fumarate, which is designated as form I. Quetiapine fumarate crystalline Form I is characterized by x-ray powder diffraction pattern having significant reflections expressed as 2θ values at about 7.3, 9.2, 11.6, 13.3, 14.4, 14.8, 15.3, 15.9, 16.2, 16.7, 17.6, 19.1, 19.7, 20.1, 20.8, 21.1, 21.8, 22.3, 23.4, 24.3, 24.7, 25.1, 25.6, 27.1, 28.5, 29.5, 33.2, 40.4 deg.

x-Ray powder diffractogram of quetiapine fumarate crystalline Form I is shown in FIG. 1. The major peaks and their intensities of x-ray powder diffractogram are shown in Table 1. The intensities of the reflections are expressed as percent of most intense reflection.

A further aspect of the present invention provides a process for the preparation of quetiapine fumarate crystalline Form I.

Quetiapine fumarate crystalline Form I is prepared by dissolving quetiapine free base and fumaric acid in a suitable solvent and crystallizing fumarate salt. This crystallization from the suitable solvent is an effective method of removing impurities.

A further aspect of the present invention thus provides quetiapine fumarate crystalline Form I which is substantially pure, for example at least 98% preferably at least 99%, more preferably at least 99.5% pure.

Preferably molar ratio of quetiapine free base to fumaric acid is between about 1:0.4 to about 1:1.

The suitable solvents are ketones like acetone, methyl iso butyl ketone; esters like ethyl acetate, ethyl formate, methyl acetate; and mixture thereof.

The preparation of quetiapine free base is described, for example in EP 0240228.

Crystallization of quetiapine fumarate from solution may be initiated by conventional means such as addition of a non-solvent, evaporation of solvent, cooling or seeding the solution.

The present invention also provides another novel crystalline form of quetiapine fumarate, which is designated as Form II. Quetiapine fumarate crystalline Form II is characterized by x-ray powder diffraction pattern having significant reflections expressed as 2θ values at about 4.9, 7.4, 9.2, 11.7, 13.4, 14.4, 14.9, 15.4, 15.9, 16.3, 16.7, 17.7, 18.6, 19.8, 20.2, 20.8, 21.2, 21.9, 22.4, 22.9, 23.4, 24.3, 24.7, 25.2, 25.7, 26.9, 27.8, 28.8, 29.4, 33.2, 35.9, 38.0, 38.7, 39.9, 42.8 deg.

x-Ray powder diffractogram of quetiapine fumarate Form II is shown in FIG. 2. The major peaks and their intensities of x-ray powder diffractogram are shown in table 2. The intensities of the peaks are expressed as percent of most intense reflection.

A further aspect of the present invention provides a process for the preparation of quetiapine fumarte Form II.

Quetiapine fumarate crystalline Form II is prepared by dissolving quetiapine free base in methyl tert. butyl ether, heating to reflux, adding fumaric acid at reflux, maintaining at reflux for about 30 minutes to about 1 hour, cooling to 20–30° C., maintaining for about 30 minutes with or without stirring, optionally seeding with quetiapine fumarate crystalline Form II, filtering and washing the crystals formed with methyl tert. butyl ether.

Preferably molar ratio of quetiapine free base to fumaric acid is between about 1:0.4 to about 1:1.

The present invention also provides a novel amorphous form of quetiapine fumarate, which is designated as amorphous quetiapine fumarate. The amorphous quetiapine fumarate is characterized by having broad x-ray diffraction maximum expressed as 2θ between about 10 and about 30 deg.

A further aspect of the present invention provides a process for the preparation of amorphous quetiapine fumarate. Amorphous quetiapine fumarate may be prepared by dissolving quetiapine fumarate in a solvent mixture, removing the solvent from the solution. Quetiapine fumarate crystalline Form I or Form II, which are obtained as described herein above, or quetiapine fumarate obtained by previously known methods may be used for the preparation of amorphous quetiapine fumarate.

The solvent mixture comprises chloroform and methanol in a ratio between about 1:0.5 and 1:2 volume/volume, preferably in the ratio of 1:1 volume/volume. The solvent can be removed form the solution by techniques such as vacuum drying or spray drying.

A further aspect of the present invention provides a pharmaceutical composition comprising an effective amount of quetiapine fumarate polymorphic form and a pharmaceutically acceptable carrier.

The quetiapine fumarate polymorphic forms include quetiapine fumarate crystalline Form I, quetiapine fumarate crystalline Form II and amorphous quetiapine fumarate.

Figure 1:
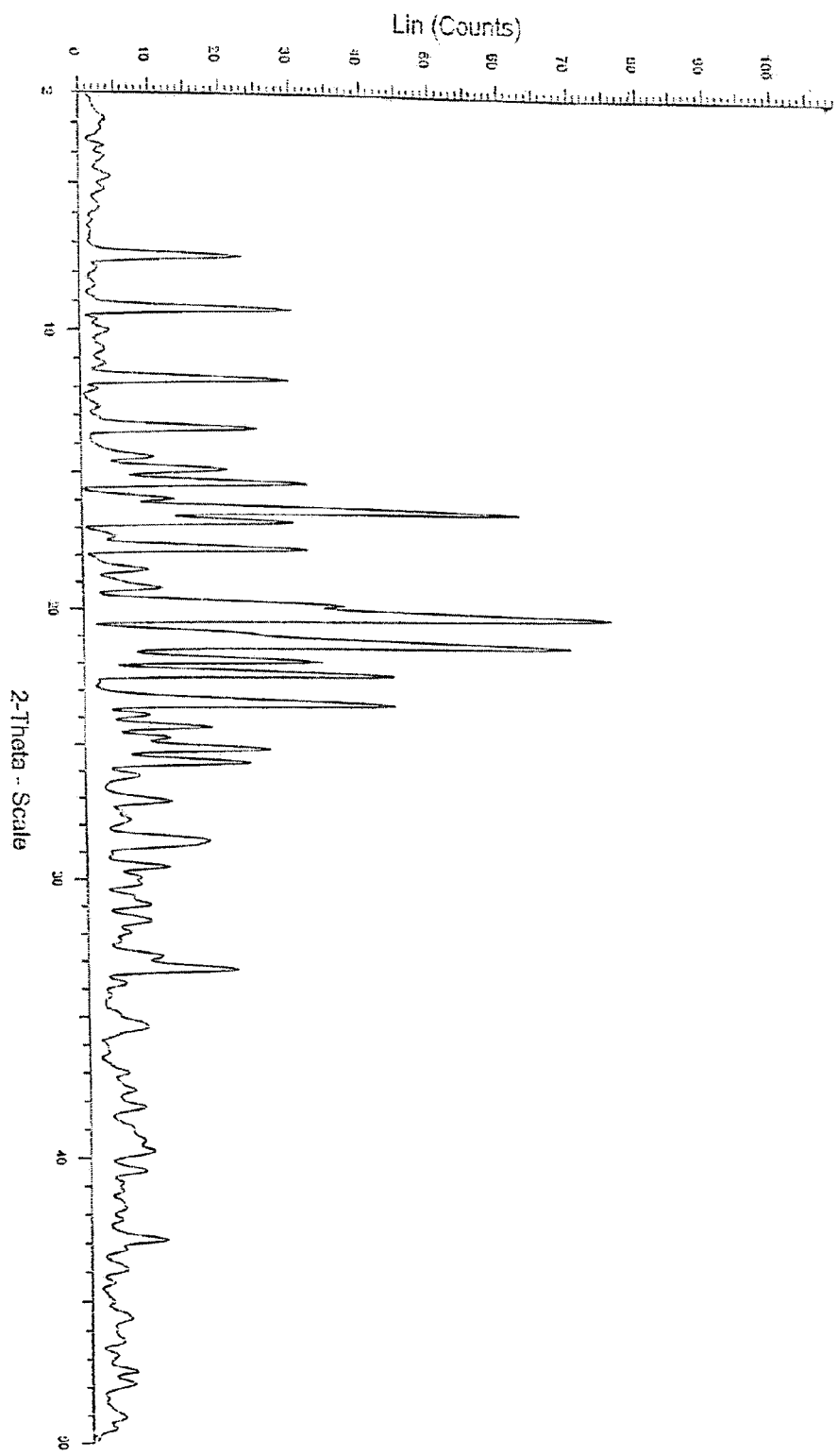
FIG. 1 is x-ray powder diffraction pattern of quetiapine fumarate crystalline Form I.

The x-ray powder diffraction spectra was measured on a Siemens D-5000 diffractometer.

TABLE 1

| 2θ (degree) | % Intensity |
| --- | --- |
| 7.3 | 30.4 |
| 9.2 | 39.9 |
| 11.6 | 39.3 |
| 13.3 | 33.1 |
| 14.4 | 12.9 |
| 14.8 | 27.1 |
| 15.3 | 42.2 |
| 15.9 | 16.8 |
| 16.2 | 83.3 |
| 16.7 | 39.0 |
| 17.6 | 41.6 |
| 19.1 | 13.4 |
| 19.7 | 48.1 |
| 20.1 | 100.0 |
| 20.8 | 30.8 |
| 21.1 | 91.8 |
| 21.8 | 43.3 |
| 22.3 | 57.2 |
| 23.4 | 57.2 |
| 24.3 | 21.7 |
| 24.7 | 13.8 |
| 25.1 | 32.6 |
| 25.6 | 28.9 |
| 27.1 | 13.7 |
| 28.5 | 20.4 |
| 29.5 | 13.0 |
| 33.2 | 26.3 |
| 40.4 | 13.0 |

TABLE 2

| 2θ (degree) | % Intensity |
| --- | --- |
| 4.9 | 9.9 |
| 7.4 | 24.0 |
| 9.2 | 41.0 |
| 11.7 | 37.7 |
| 13.4 | 25.5 |
| 14.4 | 22.2 |
| 14.9 | 32.0 |
| 15.4 | 33.2 |
| 15.9 | 25.2 |
| 16.3 | 52.5 |
| 16.7 | 36.4 |
| 17.7 | 28.4 |
| 18.6 | 22.3 |
| 19.8 | 53.1 |
| 20.2 | 82.2 |
| 20.8 | 24.7 |
| 21.2 | 77.3 |
| 21.9 | 41.8 |
| 22.4 | 43.6 |
| 22.9 | 100.0 |
| 23.4 | 49.5 |
| 24.3 | 20.2 |
| 24.7 | 20.4 |
| 25.2 | 24.7 |

TABLE 2-continued

| 2θ (degree) | % Intensity |
| --- | --- |
| 25.7 | 38.5 |
| 26.9 | 25.4 |
| 27.8 | 20.2 |
| 28.8 | 80.8 |
| 29.4 | 53.2 |
| 33.2 | 23.8 |
| 35.9 | 11.8 |
| 38.0 | 28.7 |
| 38.7 | 24.9 |
| 39.9 | 13.8 |
| 42.8 | 14.3 |

The following examples are presented for illustrative purposes only and are not intended as a restriction on the scope of the invention.

EXAMPLE 1

Quetiapine free base (5 gm) obtained by the process described in EP 0240228 (example 1) is dissolved in acetone (60 ml). To this solution, fumaric acid (0.9 gm) is added and then heated for complete dissolution. The solution is cooled to 20 to 25° C. and maintained for 1 hour. The product obtained is filtered washed with acetone and dried to give 4.9 gm of quetiapine fumarate Form I. (HPLC purity: 99.8%).

EXAMPLE 2

Example 1 is repeated using 60 ml ethyl acetate instead of acetone. Yield of quetiapine fumarate Form I is 5.2 gm (HPLC purity: 99.6%).

EXAMPLE 3

Example 1 is repeated by seeding the solution with quetiapine fumarate Form 1 during maintenance at 20 to 25° C. Yield of quetiapine fumarate Form I is 5.2 gm (HPLC purity: 99.8%).

EXAMPLE 4

Quetiapine free base (10 gm), obtained by the process described in example 1 of EP 0240228 is dissolved in methyl tert. butyl ether (100 ml). The solution is heated to reflux and fumaric acid (1.5 gm) is added at reflux. The refluxing is continued for 45 minutes, cooled to 20–25° C. and stirred for 30 minutes. The resulting crystals are filtered washed with methyl tert. butyl ether and dried to give 19.2 gm of quetiapine fumarate Form II.

EXAMPLE 5

Example 4 is repeated by seeding the contents during maintenance at 20 to 25° C. with quetiapine fumarate Form II. The yield of quetiapine fumarate Form II is 19.5 gm.

EXAMPLE 6

Quetiapine fumarate (2 gm) obtained by the process described in example 4 of EP 0240228 added to a solvent mixture containing methanol (10 ml) and chloroform (10 ml). The contents are heated to 40–45° C. for dissolution and the clear solution is subjected to vacuum drying at 35–40° C. for 15 to 20 hours to give 1.9 gm of amorphous quetiapine fumarate.

EXAMPLE 7

Example 6 is repeated using quetiapine fumarate Form I instead of quetiapine fumarate. The yield of amorphous quetiapine fumarate is 1.8 gm.

EXAMPLE 8

Example 6 is repeated by subjecting the clear solution to spray drying instead of vacuum drying to give 1.8 gm of amorphous quetiapine fumarate.

We claim:

1. Quetiapine fumarate crystalline Form I having an x-ray powder diffractogram having peaks expressed as 2θ values at about 7.3, 9.2, 11.6, 13.3, 14.4, 14.8, 15.3, 15.9, 16.2, 16.7, 17.6, 19.1, 19.7, 20.1, 20.8, 21.1, 21.8, 22.3, 23.4, 24.3, 24.7, 25.1, 25.6, 27.1, 28.5, 29.5, 33.2, and 40.4 degrees.

2. Quetiapine fumarate crystalline Form I having an x-ray powder diffractogram as shown in FIG. 1.

3. A process for preparation of quetiapine fumarate Form I as defined in claim 1, which comprises the steps of:
 a) dissolving quetiapine free base and fumaric acid in a suitable solvent; and
 b) crystallizing quetiapine fumarate Form I from the solution formed in step (a).

4. A process according to claim 3 wherein the suitable solvent is selected from the group consisting of acetone, methyl isobutyl ketone, ethyl acetate, ethyl formate and methyl acetate.

5. A process according to claim 3 wherein the suitable solvent is acetone.

6. A process according to claim 3 wherein the suitable solvent is ethylacetate.

7. A process according to claim 3 wherein the crystallization is initiated by seeding with quetiapine fumarate Form I.

8. A process according to claim 4 wherein the crystallization is initiated by seeding with quetiapine fumarate Form I.

9. Quetiapine fumarate crystalline Form II having an x-ray powder diffractogram having peaks expressed as 2θ values at about 4.9, 7.4, 9.2, 11.7, 13.4, 14.4, 14.9, 15.4, 15.9, 16.3, 16.7, 17.7, 18.6, 19.8, 20.2, 20.8, 21.2, 21.9, 22.4, 22.9, 23.4, 24.3, 24.7, 25.2, 25.7, 26.9, 27.8, 28.8, 29.4, 33.2, 35.9, 38.0, 38.7, 39.9, and 42.8 degrees.

Figure 2:
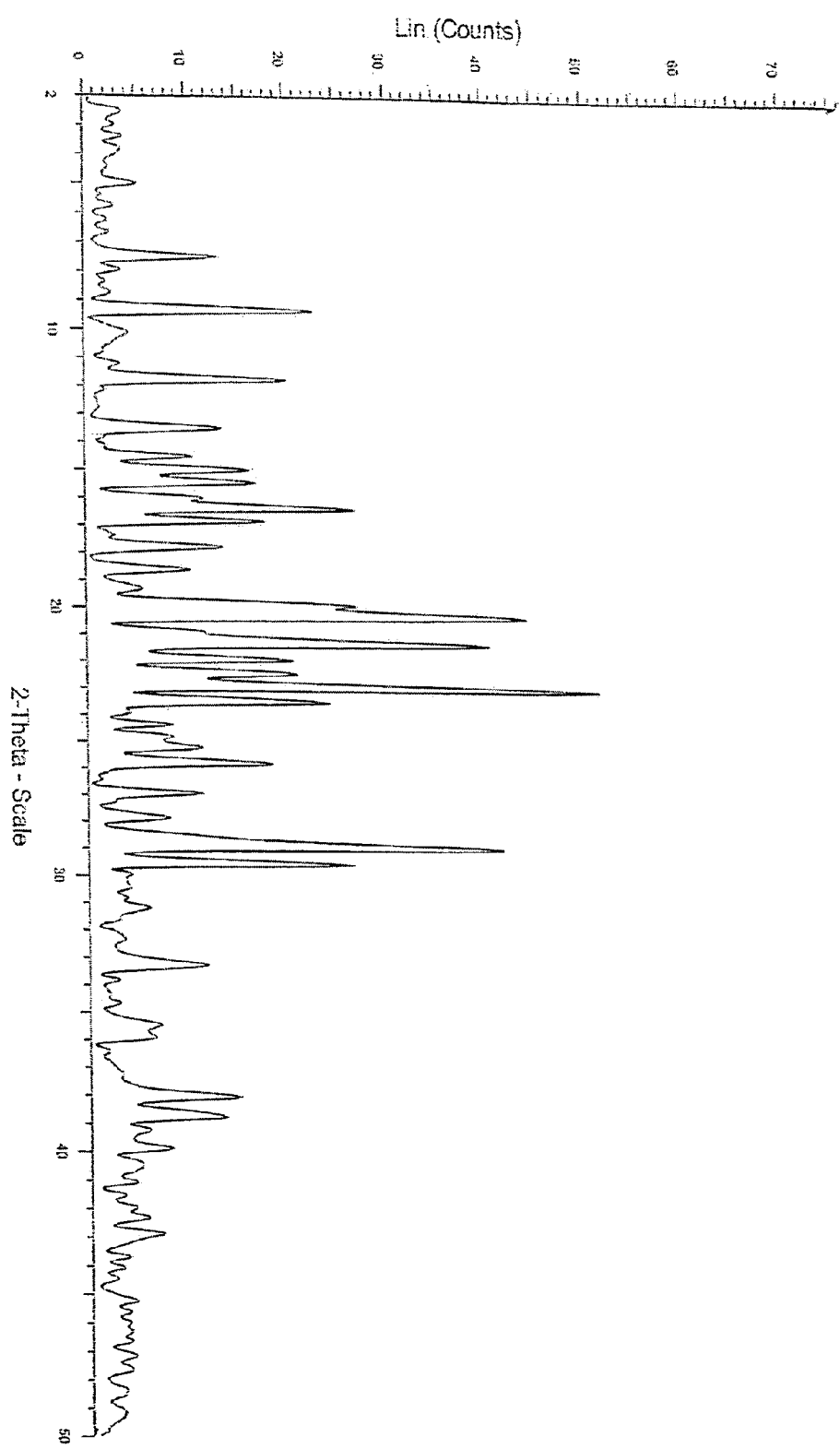
FIG. 2 is x-ray powder diffraction pattern of quetiapine fumarate crystalline Form II.

10. Quetiapine fumarate crystalline Form II having an x-ray powder diffractogram as shown in FIG. 2.

11. A process for preparation of quetiapine fumarate crystalline Form II as defined in claim 9, which comprises the steps of dissolving quetiapine free base in methyl tert, butyl ethers, heating to reflux, adding fumaric acid at reflux, maintaining at reflux for about 30 minutes to about 1 hour, cooling to about 20 to 30° C., maintaining for about 30 minutes with or without stirring, optionally seeding, and collecting the quetiapine fumarate Form II crystals formed.

12. A process according to claim 11, wherein the solution is seeded with quetiapine fumarate Form II.

13. Amorphous quetiapine fumarate having an x-ray powder diffractogram having a maximum expressed as 2θ values at about 10 to about 30 degrees.

Figure 3:
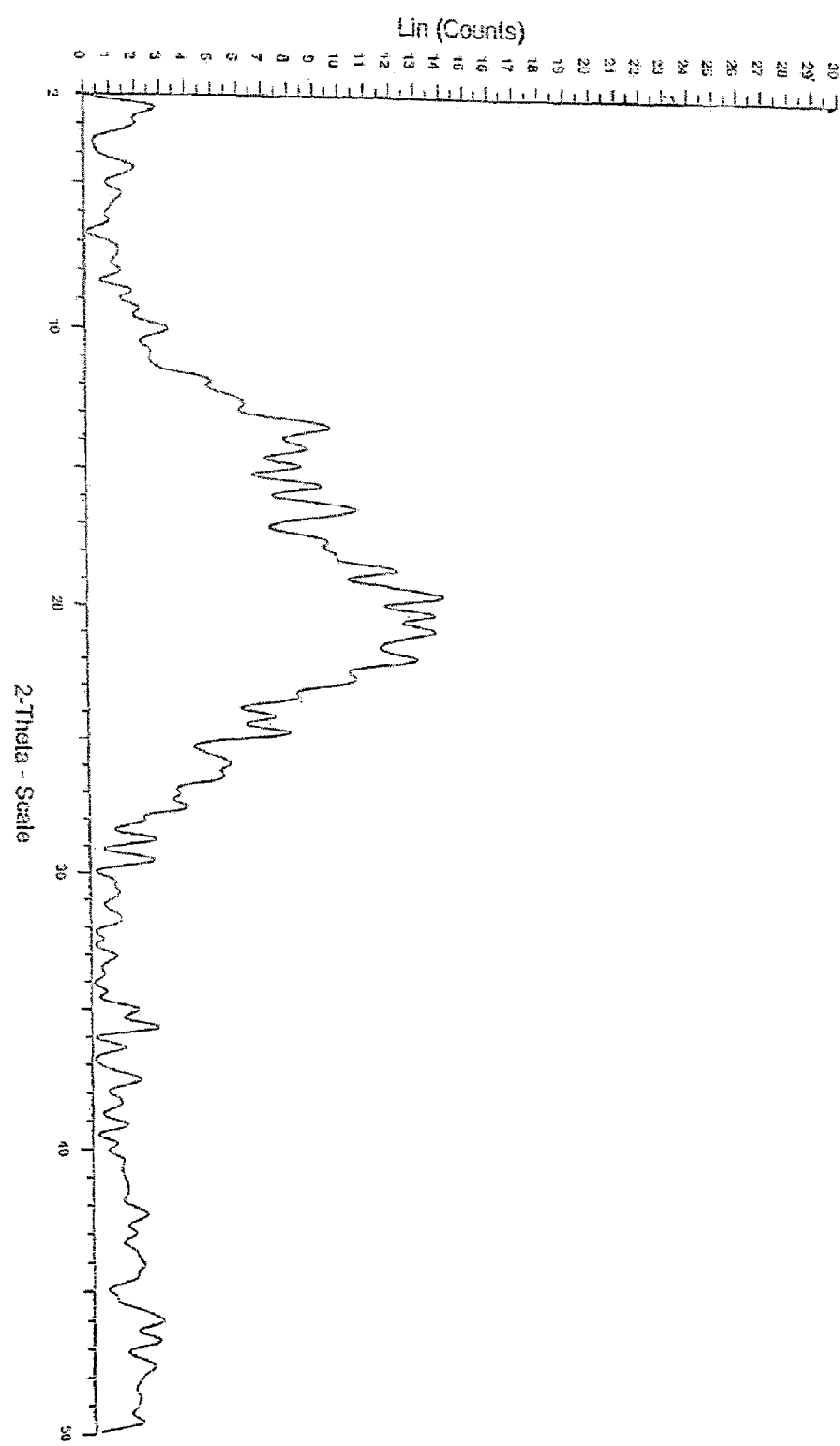
FIG. 3 is x-ray powder diffractogram of amorphous quetiapine fumarate.

14. Amorphous quetiapine fumarate having an x-ray powder diffractogram as shown in FIG. 3.

15. A process for preparation of amorphous quetiapine fumarate having an x-ray powder diffractogram having a maximum expressed as 2θ values at about 10 to about 30 degrees, which comprises the steps of:
 a) dissolving quetiapine fumarate in a solvent mixture of chloroform and methanol; and
 b) removing the solvents from the solution formed in step (a) by drying.

16. A process according to claim 15, wherein the solvents are removed by vacuum drying.

17. A process according to claim 15, wherein the solvents are removed by spray drying.

* * * * *

UNITED STATES PATENT AND TRADEMARK OFFICE
CERTIFICATE OF CORRECTION

PATENT NO. : 7,238,686 B2  Page 1 of 1
APPLICATION NO. : 10/488628
DATED : July 3, 2007
INVENTOR(S) : Bandi Parthasaradhi Reddy et al.

It is certified that error appears in the above-identified patent and that said Letters Patent is hereby corrected as shown below:

Title Page, Item (12)
Delete "Parthasaradhi et al." and replace with --Parthasaradhi Reddy et al.--.

Title Page, Item (75) Inventors, Should Read: --Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)--.

Signed and Sealed this

Seventeenth Day of June, 2008

JON W. DUDAS
*Director of the United States Patent and Trademark Office*